(12) United States Patent
Costanzo

(10) Patent No.: US 11,213,332 B2
(45) Date of Patent: Jan. 4, 2022

(54) BONE FIXATION ELEMENT

(71) Applicant: DePuy Synthes Products, Inc., Raynham, MA (US)

(72) Inventor: Joseph Costanzo, Green Lane, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 132 days.

(21) Appl. No.: 16/572,754

(22) Filed: Sep. 17, 2019

(65) Prior Publication Data

US 2021/0077169 A1    Mar. 18, 2021

(51) Int. Cl.
| | | |
|---|---|---|
| A61B 17/86 | (2006.01) | |
| A61B 17/88 | (2006.01) | |
| A61B 17/64 | (2006.01) | |
| A61B 17/68 | (2006.01) | |

(52) U.S. Cl.
CPC ...... *A61B 17/8819* (2013.01); *A61B 17/6475* (2013.01); *A61B 17/864* (2013.01); *A61B 2017/681* (2013.01)

(58) Field of Classification Search
CPC .................................................. A61B 17/864
See application file for complete search history.

(56) References Cited

U.S. PATENT DOCUMENTS

| | | | | |
|---|---|---|---|---|
| 6,048,343 | A  * | 4/2000 | Mathis ............... | A61B 17/7098 606/304 |
| 8,974,505 | B2 * | 3/2015 | Sawa ................. | A61B 17/7098 606/304 |
| 2005/0021084 | A1* | 1/2005 | Lu ....................... | A61B 17/864 606/218 |
| 2011/0015684 | A1* | 1/2011 | Belcheva ............. | A61B 17/864 606/314 |
| 2012/0041395 | A1* | 2/2012 | Sweeney .............. | A61B 17/864 604/272 |
| 2013/0144344 | A1* | 6/2013 | Giancola .............. | A61B 17/742 606/304 |
| 2015/0272646 | A1* | 10/2015 | Russell .............. | A61B 17/8695 606/304 |

* cited by examiner

*Primary Examiner* — Nicholas W Woodall
(74) *Attorney, Agent, or Firm* — BakerHostetler

(57) ABSTRACT

A bone fixation element is described. The bone fixation element includes first and second channels, a connection channel, and at least one fenestration. The first channel includes a first proximal channel portion and a first distal channel portion. The first proximal channel portion extends from a proximal end of the first channel toward a distal end, and the first distal channel portion extends from the first proximal channel portion to the distal end. The connection channel extends between the distal end of the first channel and a distal end of the second channel such that the first channel is in fluid communication with the second channel via the connection channel. The at least one fenestration extends from at least one of the first and second channels to an outer surface of the bone fixation element.

26 Claims, 12 Drawing Sheets

BONE FIXATION ELEMENT

TECHNICAL FIELD

This disclosure relates generally to a bone fixation element and, more particularly, to a bone fixation element with cannulae for delivery and removal of material at or near an anchor location of the element.

BACKGROUND

Bone fixation elements can be used for anchoring external fixation components on the bone. An example of a bone fixation element is a bone screw. During a medical procedure, such as fracture fixation, bone screws are used within a framework of one or more members to anchor external setting components. Bone screws are anchored into the bone after being inserted through small incisions in the skin and soft tissue. Bone screws include threads for anchoring the screw in the bone and to prevent axial slippage of the screw relative to the bone. The external setting components are mounted on a shaft of the screw after the screw has been anchored.

A disadvantage of anchoring bone screws to a bone is the danger of infection from local necrosis and environmental exposure. The insertion of the screw through the skin leaves a tract for bacteria to invade. Infections can cause the screw-bone interface to become loose, which can result in regular tightening of the screw, removal and re-setting of the screw, and/or regular treatment and cleaning from around where the screw enters the skin to the screw-bone interface. Techniques to overcome the dangers of infection include permanently affixing the bone screws to the bone by preventing removal of the screw, inserting the bone screw in an under-dimensioned hole in the bone, or by applying osteoinductive coatings, such as hydroxyapatite (HA). However, these techniques make it difficult to anchor and remove the bone screw during and after completion of the medical procedure, and they often still require regular treatment and cleaning. Therefore, a bone screw that can be effectively anchored and removed and that can also prevent and/or limit pin tract infections is desired.

The foregoing background discussion is intended solely to aid the reader. It is not intended to limit the innovations described herein. Thus, the foregoing discussion should not be taken to indicate that any particular element of a prior system is unsuitable for use with the innovations described herein, nor is it intended to indicate that any element is essential in implementing the innovations described herein.

SUMMARY

The foregoing needs are met, to a great extent, by the bone screw disclosed in the present application.

An aspect of the present disclosure provides a bone fixation element. The bone fixation element comprises a shaft and a tip region configured to be driven into bone. The tip region defines a distal end of the bone fixation element. The shaft defines an external surface and extends from the tip region in a proximal direction. The bone fixation element defines 1) first and second channel segments each having a first end open to the external surface of the shaft, and a second end opposite the first end, and 2) a connection channel segment that extends from the first channel segment to the second channel segment so as to place the first channel segment in fluid communication with the second channel segment. The bone fixation element further defines at least one aperture that extends from at least one of the first and second channel segments to the external surface of the shaft so as to place at least one of the first and second channel segments in fluid communication with an external environment of the shaft.

Another aspect of the present disclosure provides a Schanz screw for removal of necrotic tissue. The Schanz screw comprises a first channel, a second channel, a connection channel, and at least one fenestration. The first channel extends from a proximal end to a distal end, and includes a first proximal channel portion and a second proximal channel portion. The first proximal channel portion extends from the proximal end toward the distal end, and the first distal channel portion extends from the first proximal channel portion toward the distal end. The second channel extends from a proximal end to a distal end. The connection channel extends between the first channel and the second channel such that the first channel is in fluid communication with the second channel via the connection channel. The at least one fenestration extends from the first distal channel portion to an outer surface of the screw. The first channel and the second channel are configured such that when a suction force is applied to the proximal end of the first channel to pull a fluid through the screw from the second channel to the first channel a venturi effect occurs that draws the necrotic tissue into the at least one fenestration.

Another aspect of the present disclosure includes a method of infection prevention using a screw. The screw includes a first channel, a second channel, a connection channel that extends between a distal end of the first channel and a distal end of the second channel, and at least one fenestration that extends from at least one of the first channel and the second channel to an outer surface of the screw. The method comprises: providing a suction force to a proximal end of the first channel to pull a first fluid through the screw from the second channel, wherein the suction force causes a venturi effect to occur within the screw that draws a second fluid into the first channel through the at least one fenestration.

This summary is provided to introduce a selection of concepts in a simplified form that are further described below in the Detailed Description section. This Summary is not intended to identify key features or essential features of the claimed subject matter, nor is it intended to be used to limit the scope of the claimed subject matter. Furthermore, the claimed subject matter is not constrained to limitations that solve any or all disadvantages noted in any part of this disclosure.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there are shown in the drawings illustrative embodiments of the disclosure. It should be understood, however, that the application is not limited to the precise arrangements and instrumentalities shown. In the drawings.

DETAILED DESCRIPTION

Figure 1:
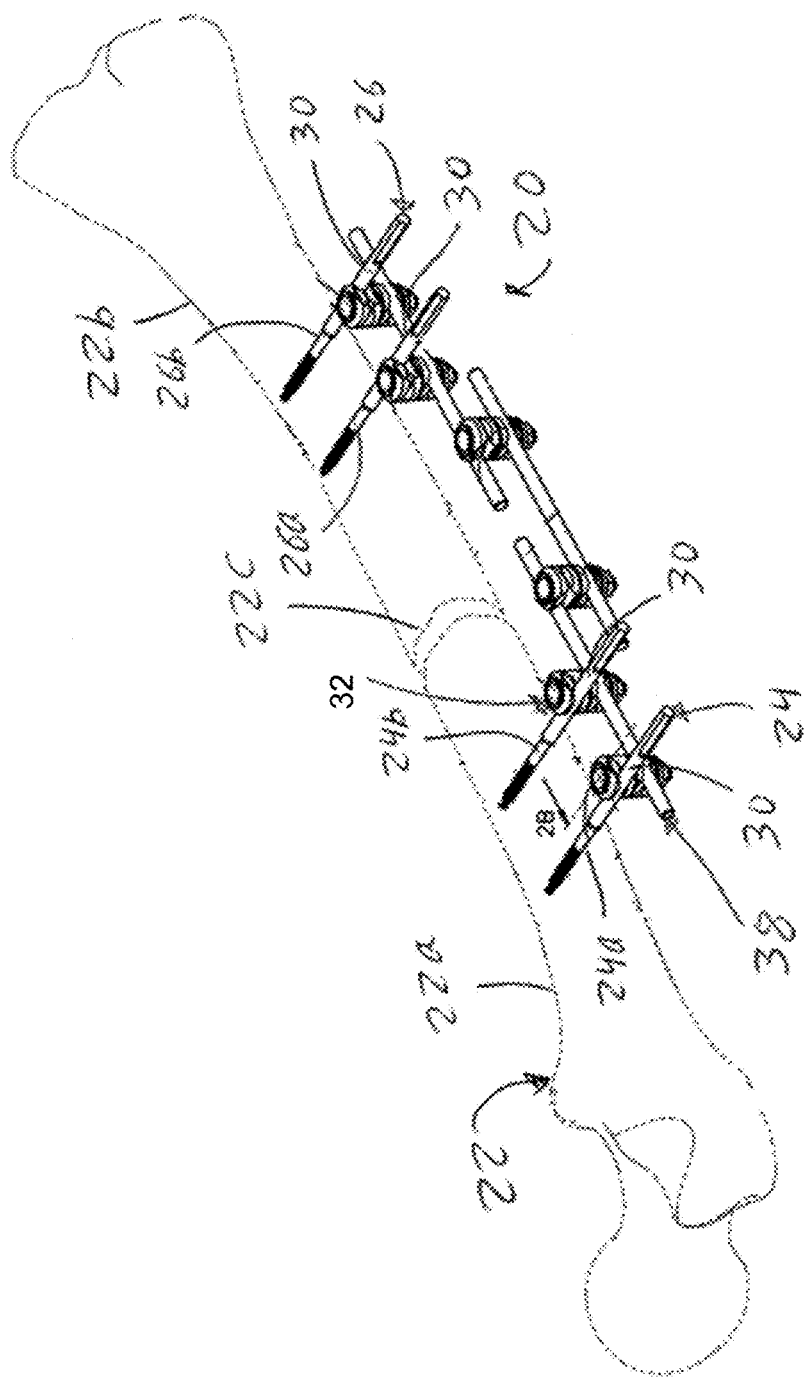
FIG. 1 illustrates an external fixation assembly anchored into a bone, according to an aspect of this disclosure.

A bone screw for anchoring to a bone is disclosed. The bone screw includes two cannulae that extend from a proximal end of the bone screw toward a distal end of the bone screw. A channel is positioned between the two cannulae to provide fluid communication therebetween. At least one of the two cannulae includes a venturi region in a location on the bone screw that engages the bone and/or soft tissue. The venturi region of the at least one cannulae includes fenestrations that extend to an exterior of the screw. After the screw is anchored to the bone, a suction force is provided to one of the two cannulae (while the other cannula and body remain at ambient atmospheric pressure) to create a vacuum within the screw to pull a fluid through the two cannulae and the connection channel. The flow of the fluid through the two cannulae and the connection channel creates a venturi effect within the venturi region, which produces a suction force through the fenestrations and into the two cannulae. The suction force through the fenestrations allows for necrotic tissue debris near or around the location of the anchor point of the bone screw to be removed.

Certain terminology used in this description is for convenience only and is not limiting. The words "top", "bottom", "distal", "proximal", "above", "below", "axial", "transverse", "circumferential," and "radial" designate directions in the drawings to which reference is made. The term "substantially" and derivatives thereof, and words of similar import, when used to described sizes, shapes, spatial relationships, distances, directions, and other similar parameters includes the stated parameter in addition to a range up to 10% more and up to 10% less than the stated parameter, including 5% more and 5% less, including 3% more and 3% less, including 1% more and 1% less. All ranges disclosed herein are inclusive of the recited endpoint and independently combinable (for example, the range of "from 2 grams to 10 grams" is inclusive of the endpoints, 2 grams and 10 grams, and all the intermediate values). The terminology includes the above-listed words, derivatives thereof and words of similar import.

The bone fixation elements described herein can be used in, for example, in fracture fixation to internally stabilize and/or join bones, e.g., fractured or broken bones, either in conjunction with mechanical devices, such as metal plates, pins, rods, wires, or individually. The bone fixation elements may include, for example, small fragment screws, cortex screws, cancellous screws, dynamic hip screws, lag screw, malleolar screws, Schanz screws, Steinmann pins, or still other types of screws and/or pins. The size and function of the bone fixation elements described herein may vary depending on the intended use. The head of the bone fixation element may be modified in order to operate with any of a number of appropriate drivers and drills known in the art. The head may also provide fluid coupling geometry.

Referring to FIG. 1, a bone implant, such as an external fixation system 20, is configured to stably support a second bone segment 22b relative to a first bone segment 22a. The first and second bone segments can be of the same bone or of different bones. In accordance with the illustrated embodiment, the first and second bone segments 22a-b are of a bone, such as a long bone 22, and are separated from each other by a bone gap 22c, such as a fracture, of the long bone 22. The external fixation system 20 can include at least one external fixation bone element 24 configured to attach to bone, for instance at the first bone segment 22a, and at least one external fixation bone element 26 configured to attach to bone, for instance at the second bone segment 22b. In accordance with the illustrated embodiment, the at least one bone fixation element 24 can include first and second bone anchors 24a and 24b that are configured to attach to the same bone segment, for instance to the first bone segment 22a, and the at least one bone fixation element 26 can include first and second bone anchors 26a and 26b that are configured to attach to the same bone segment, for instance to the second bone segment 22b.

The external fixation system 20 further includes at least one bone fixation clamp 32 configured to attach to a first one of the bone fixation elements 24a-b and 26a-b. The clamp 32 is further configured to attach to the at least one support rod 38 so as to fixedly secure the attached bone fixation elements to the at least one support rod 38. In accordance with the illustrated embodiment, the at least one clamp 32 is configured to attach to any of the bone fixation elements 24 and 26. In accordance with the illustrated embodiment, one clamp 32 is attached to the first bone element 24a and a second clamp 32 is attached to the second bone element 24b. Further, in accordance with the illustrated embodiment, the at least one clamp 32 can include a first clamp and second clamp each configured to attach to any of the bone fixation elements 24 and 26 and/or the at least one support rod 38. The clamp 32 is further configured to attach to the bone fixation elements 24 and 26 to the respective shafts 30, for instance at the respective unthreaded external surfaces of the bone fixation elements 24 and 26.

Figure 2:
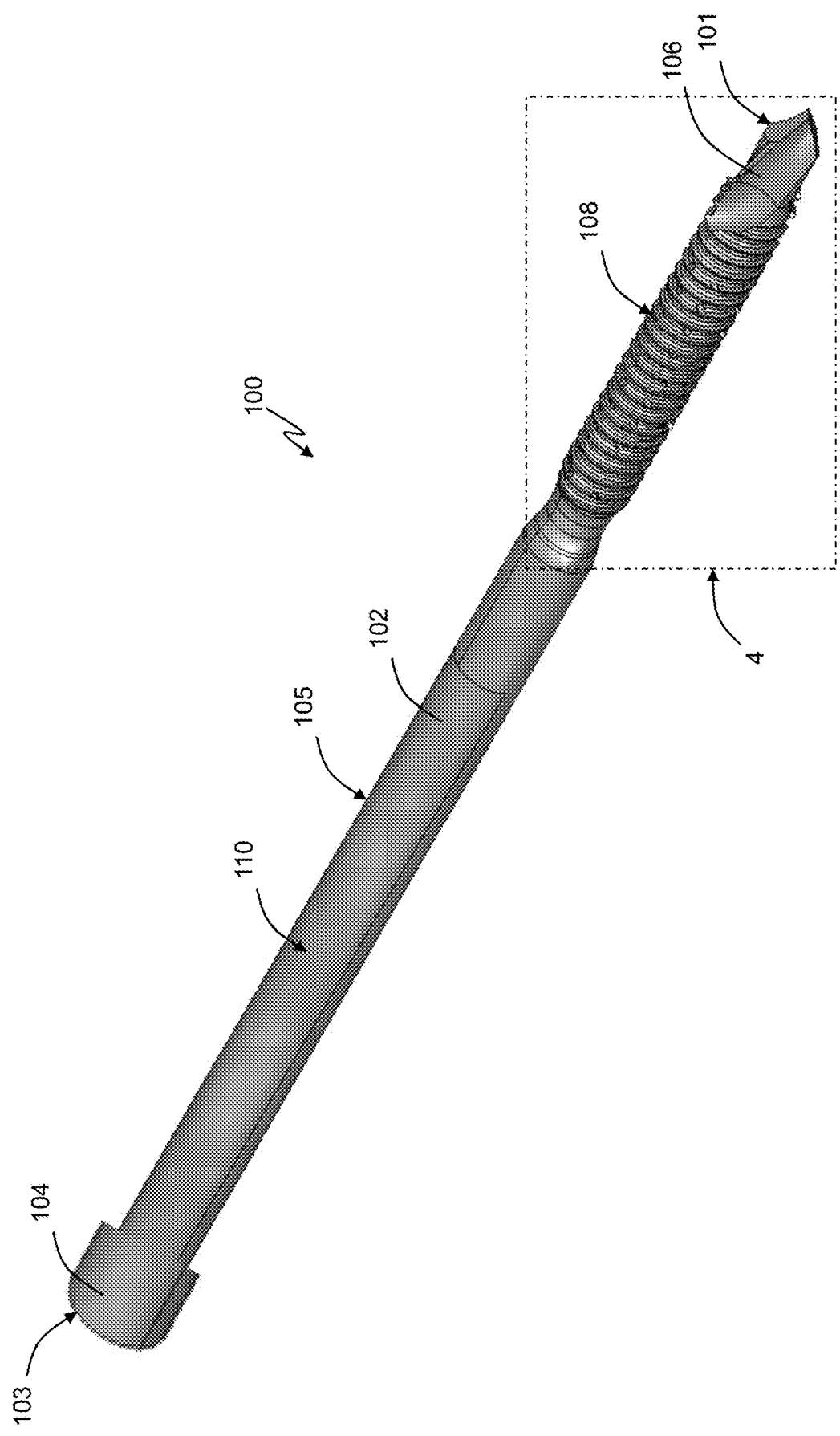
FIG. 2 is a top perspective view of a bone screw, according to an aspect of this disclosure.
Figure 3:
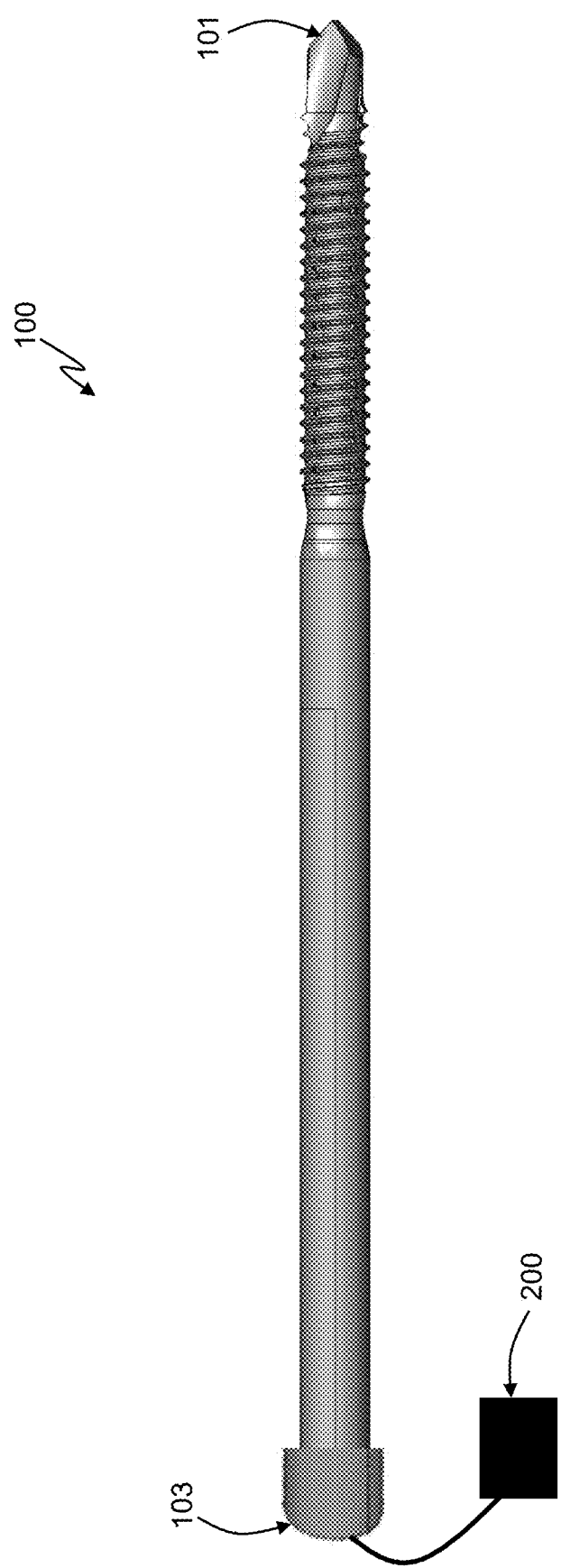
FIG. 3 is a side view of the bone screw shown in FIG. 2, according to an aspect of this disclosure.

FIGS. 2 and 3 illustrate a perspective view and a side view of a bone fixation element 100, respectively, according to aspects of this disclosure. The bone fixation element 100 may include a head 104 located at a proximal end 103 and a tip region 106 that defines a distal end 101 of the fixation element 100. The bone fixation element 100 includes a shaft 105 that extends from the tip region 106 in a proximal direction toward the proximal end 103 of the fixation element 100. The shaft 105 defines an external surface 102. In an aspect, the bone fixation element 100 may comprise a bone screw. The external surface 102 includes a threaded region 108 and an unthreaded region 110, both positioned between the head 104 and the tip region 106 along a length of the fixation element 100. The threaded region 108 extends from the tip region 106 to the unthreaded region 110. The unthreaded region 110 extends from the threaded region 108 to the head 104. In an aspect, the threaded region 108 and the tip region 106 may overlap, such that at least a portion of the tip region 106 includes threads. In an alternative aspect, the bone fixation element 100 may comprise a pin that has an external surface 102 that is unthreaded along its length between its proximal and distal ends. In another alternative aspect, the bone fixation element 100 may comprise a threaded region 108 in a center of the shaft 105 such that unthreaded regions are located distally and proximally relative to the threaded region 108. In another alternative aspect, the threaded region 108 may extend from the tip region 106 to the head 104 at the proximal end 103.

Figure 4:
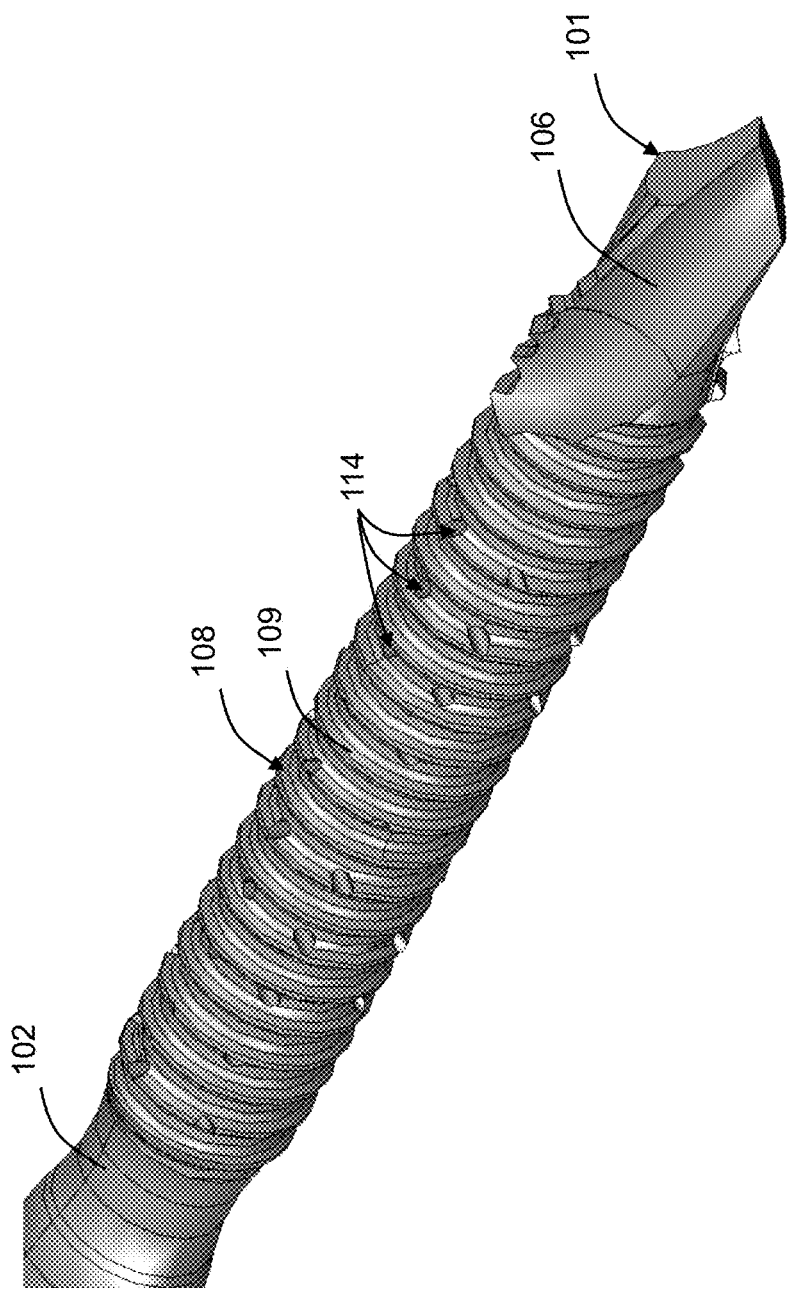
FIG. 4 is a close-up view of the top perspective view of the bone screw shown in FIG. 2, according to an aspect of this disclosure.

FIG. 4 illustrates a close-up perspective view (designated by reference number 4 in FIG. 2) of the threaded region 108 and the tip region 106 of the fixation element 100. The tip region 106 may be configured to be self-cutting and/or self-tapping to facilitate the insertion of the fixation element 100 into a bone. For example, the tip region 106 may be in the form of one or more cutting flutes or grooves radially distributed over a circumference of the tip region 106. The tip region 106 is configured to expand a hole in the bone to approximately a minor diameter of the bone fixation element 100.

The threaded region 108 is configured to engage a wall of the hole formed in the bone by the tip region 106. The threaded region 108 includes threads 109 that extend about the external surface 102 of the threaded region 108. Rotation of the fixation element 100 causes the threaded region 108 to drive the fixation element 100 into the hole of the bone. The threaded region 108 includes the minor diameter and a major diameter. The minor diameter of the threaded portion 108 defines the minor diameter of the bone fixation element 100. The major diameter may be substantially similar to an outer diameter of the unthreaded region 110. It will be appreciated that the major diameter and the outer diameter of the unthreaded region 110 may vary by up to 10%. The external surface 102 is substantially circular in cross section. For example, if the threads 109 are removed from the external surface 102, the unthreaded region 110 and the threaded region 108 would be substantially cylindrical.

The threaded region 108 includes one or more openings 114 (e.g. apertures or fenestrations) along the external surface 102. The openings 114 may be positioned along a length of the threaded region 108 from the tip region 106 to the unthreaded region 110. The openings 114 may also be positioned circumferentially about the external surface 102. In an aspect, two or more of the openings 114 may be positioned linearly relative to one another along the external surface 102 such that each of the two or more openings 114 is positioned along a line that is substantially parallel to a central longitudinal axis 10 (see FIG. 7) of the fixation element 100. In an aspect, each of the two or more openings 114 extend in a direction that is substantially perpendicular to the central longitudinal axis 10. The central longitudinal axis 10 extends through a center of the fixation element 100 from the proximal end 103 to the distal end 101. In an aspect, two or more openings 114 may be positioned about the central longitudinal axis 10 on a circular plane that is substantially perpendicular to the central longitudinal axis 10. Alternatively, two or more openings 114 may be positioned about the threaded region 108 forming a spiral about the central longitudinal axis. In another alternative, the threaded portion 108 may include a set of two or more openings 114 that are aligned longitudinally parallel to the central longitudinal axis 10 and a set of two or more openings 114 that are aligned circumferentially (e.g. circular or spiral). Alternatively, the threaded region 108 may include multiple sets of two or more openings 114 that are aligned longitudinally and/or multiple sets of two or more openings 114 that are aligned circumferentially. The openings 114 may extend through crests of the threads 109, roots of the threads 109, flanks of the threads 109, and/or combinations of the crests, roots, and flanks of the threads 109.

Figure 6:
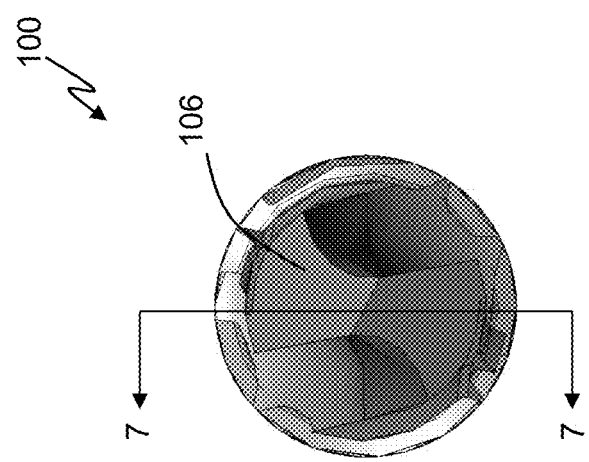
FIG. 6 is a front view of the bone screw shown in FIG. 2, according to an aspect of this disclosure.
Figure 5:
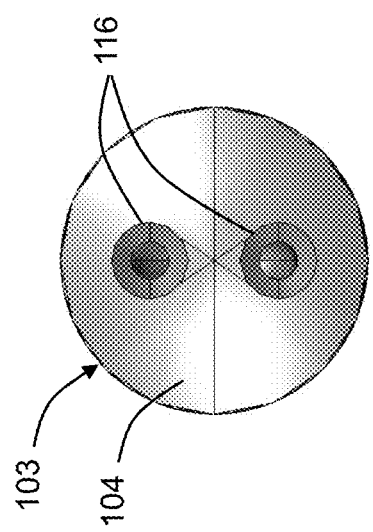
FIG. 5 is a back view of the bone screw shown in FIG. 2, according to an aspect of this disclosure.

FIG. 5 illustrates a back view of the fixation element 100 showing the head 104 located at the proximal end 103 of the fixation element 100, and FIG. 6 illustrates a front view of the fixation element 100 showing the tip region 106 at the distal end 101 of the fixation element 100. The head 104 may be substantially circular about the longitudinal axis of the fixation element 100 and may also include screw threads, to which a delivery manifold (not shown) may be attached. The head 104 includes openings 116 that provide fluid communication between an exterior of the screw and internal channels of the fixation element 100, which are described in further detail below.

Figure 7:
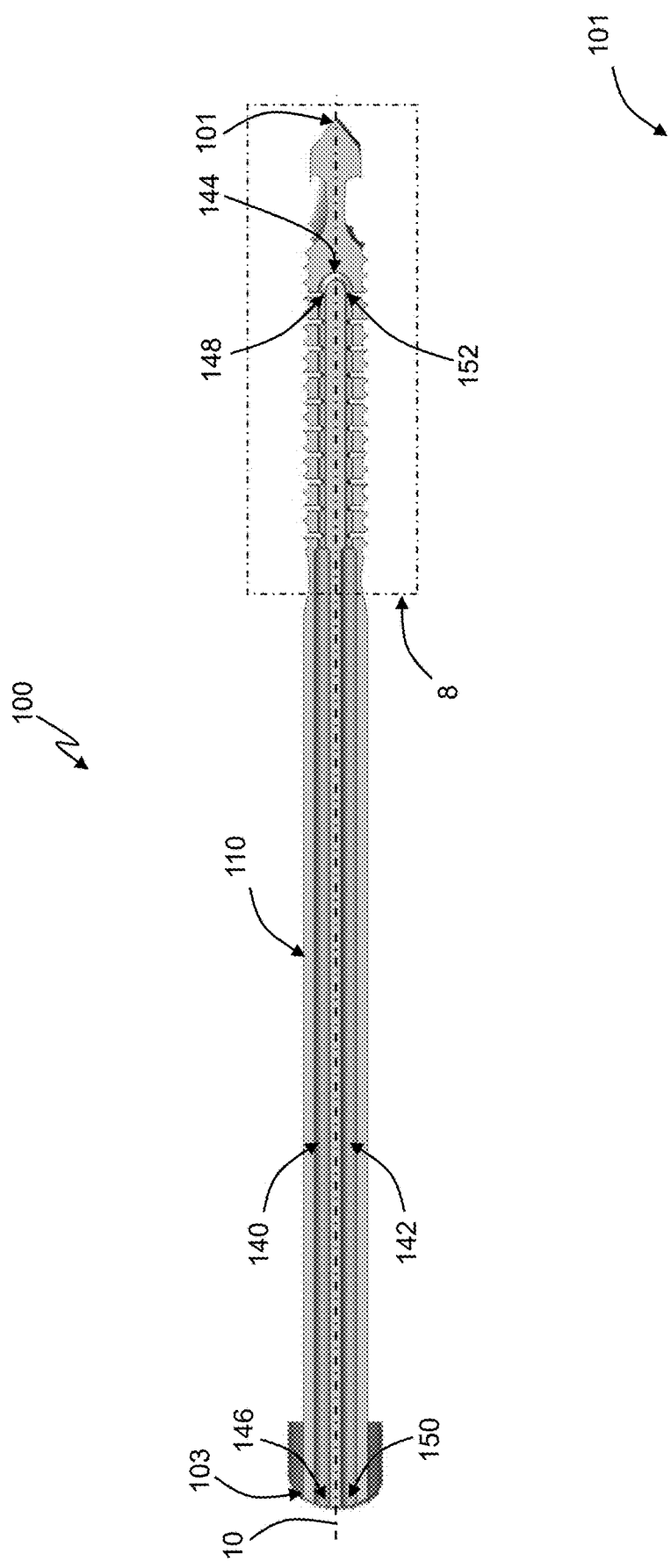
FIG. 7 is a side view of a cross section of the bone screw taken along line 7-7 of FIG. 6, according to an aspect of this disclosure.

FIG. 7 illustrates a side cross sectional view of the fixation element 100 taken along line 7-7 in FIG. 6, according to an aspect of this disclosure. The fixation element 100 defines a first channel segment 140, a second channel segment 142, and a connection channel 144. The first channel segment 140 extends from a proximal end 146 to a distal end 148, and the second channel segment 142 extends from a proximal end 150 to a distal end 152. The proximal ends 146 and 150 of both the first and second channel segments 140 and 142 are located at the proximal end 103 of the fixation element 100 and open to an exterior of the fixation element 100 through respective holes 116. The distal ends 148 and 152 of both the first and second channel segments 140 and 142 may be located proximate to the distal end 101 of the fixation element 100. The connection channel segment 144 extends between the distal end 146 of the first channel segment 140 and the distal end 152 of the second channel segment 142 such that the first channel segment 140 is in fluid communication with the second channel 142 via the connection channel 144. In an alternative aspect, the connection channel segment 144 extends between the first channel segment 140 and the second channel segment 142 at a location other than the distal end 146 of the first channel segment 140 and the distal end 152 of the second channel segment 142. In an aspect, the first channel segment 140 is substantially parallel to the second channel segment 142 along the central longitudinal axis 10. In another aspect, the first channel segment 140 is substantially symmetric to the second channel segment 142 along the central longitudinal axis 10. In another alternative aspect, the first channel segment 140 may be offset (e.g linearly or circumferentially) from the second channel segment 142 along the central longitudinal axis 10. In another alternative aspect, the first channel segment 140 and the second channel segment 142 may include cross sections that increase in size along their lengths from their respective distal ends toward their proximal ends. The cross sectional increase of the first and second channel segments 140 and 142 may help prevent clogs and facilitate removal of necrotic tissue.

Figure 8:
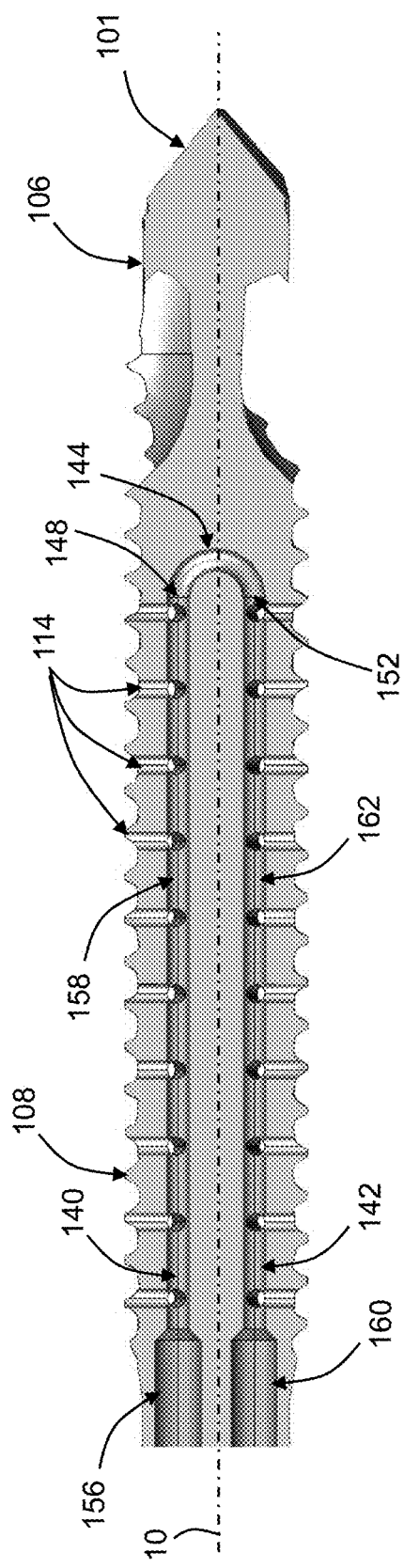
FIG. 8 is a close-up view of a cross section of the bone screw shown in FIG. 7, according to an aspect of this disclosure.

FIG. 8 illustrates a close-up side cross sectional view (designated by reference number 8 in FIG. 7) of the threaded region 108 and the tip region 106 of the fixation element 100. The first channel segment 140 includes a first proximal channel portion 156 and a first distal channel portion 158. The first proximal channel portion 156 extends from the proximal end 146 toward the distal end 148 of the first channel segment 140. The first distal channel portion 158 extends from the first proximal channel portion 156 to the distal end 148. A cross-section of the first proximal channel portion 156 is greater than a cross-section of the first distal channel portion 158. In an aspect, both of the first proximal channel portion 156 and the first distal channel portion 158 have a substantially cylindrical shape. In alternative aspects, the first proximal channel portion 156 and the first distal channel portion 158 may have cross sections that include, for example, oval shapes, rectangular shapes, or other shapes.

The first channel segment 140 may extend through the unthreaded region 110 of the fixation element 100 into the threaded region 108. In an aspect, the first distal channel portion 158 is located within the threaded region 108. In an alternative aspect, the first distal channel portion 158 may be located at least partially within the threaded region 108 and the tip region 106. In an aspect, the first proximal channel portion 156 extends through the unthreaded region 110 into the threaded region 108.

The second channel segment 142 includes a second proximal channel portion 160 and a second distal channel portion 162. The second proximal channel portion 160 extends from the proximal end 150 toward the distal end 152 of the second channel segment 142. The second distal channel portion 162 extends from the second proximal channel portion 160 to the distal end 152 of the second channel segment 142. A cross-section of the second proximal channel portion 160 may be greater than a cross-section of the second distal channel portion 162. In an aspect, both of the second proximal channel portion 160 and the second distal channel portion 162 have a substantially cylindrical shape.

The second channel segment 142 may extend through the unthreaded portion 110 of the fixation element 100 into the threaded region 108. In an aspect, the second distal channel portion 162 is located within the threaded region 108. In an alternative aspect, the second distal channel portion 162 may be located at least partially within the threaded region 108 and the tip region 106. In an aspect, the second proximal channel portion 160 extends through the unthreaded portion 110 into the threaded region 108.

One of the apertures 114 extend from the external surface 102 of the fixation element 100 to the first or second channel segments 140 and 142. Each of the channel segments 140 and 142 may include one or more apertures 114 extending to the external surface 102.

The connection channel segment 144 is positioned between the distal end 148 of the first channel segment 140 and the distal end 152 of the second channel segment 142. In alternative aspects, the connection channel segment 144 may include multiple channels positioned between the first distal channel portion 158 and the second distal channel portion 162 of the respective first and second channel segments 140 and 142. The connection channel segment 144 may have a curved cylindrical shape (see FIG. 8). For example, the connection channel segment 144 may curve distally from the first channel segment 140 toward the second channel segment 142 to an apex location, and curve proximally from the apex location to the second channel segment 142. In an aspect, the apex location is located on the central axis 10. The apex location may be located within the unthreaded region 110, the threaded region 108, or the tip region 106.

Figure 9:
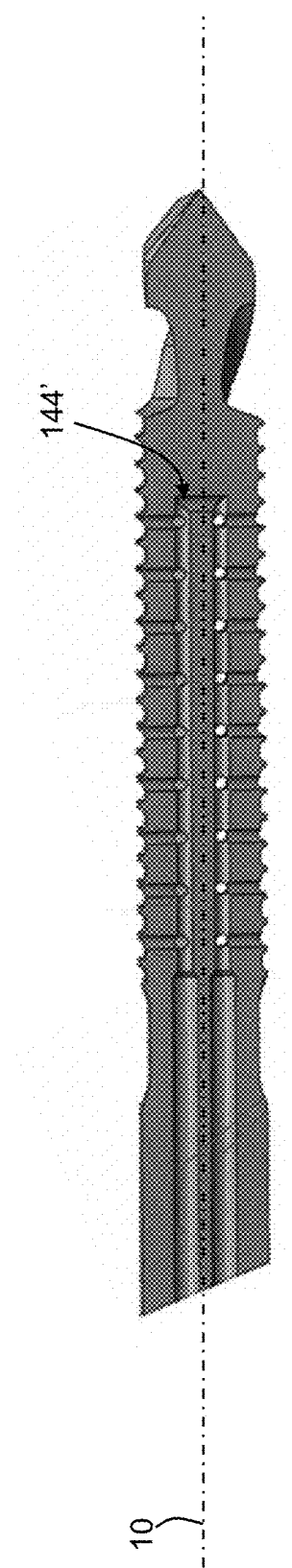
FIGS. 9-11 are close views of a cross section of a bone screw, according to alternative aspects of this disclosure.
Figure 10:
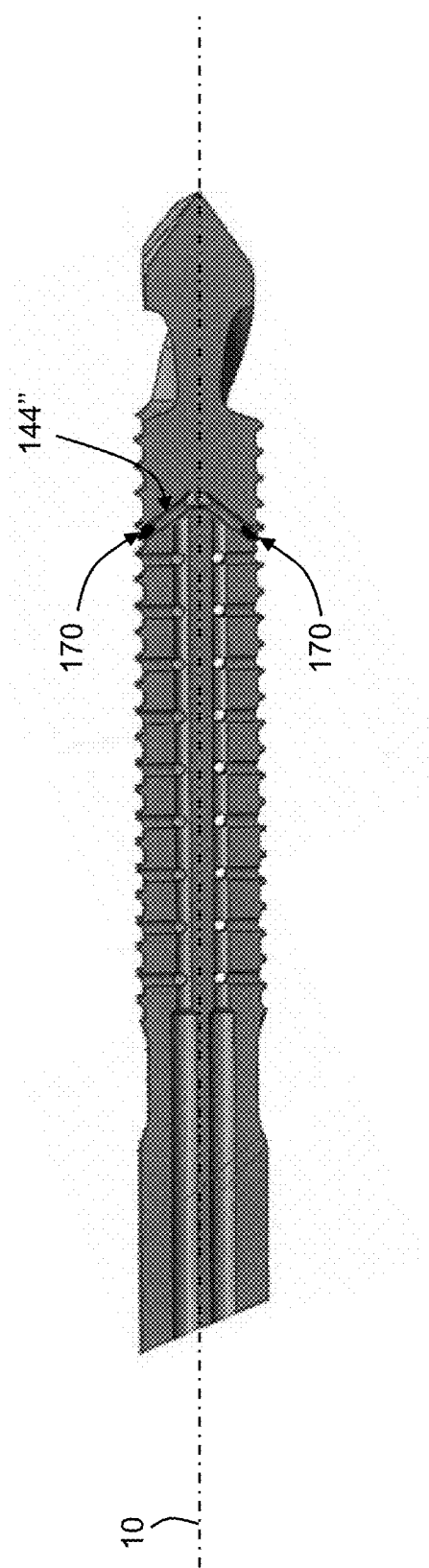
Figure 11:
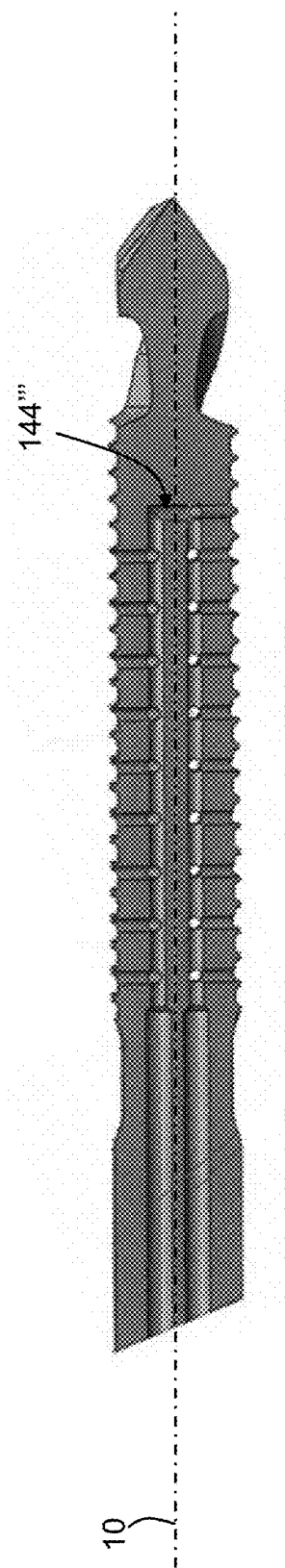

FIGS. 9-11 illustrate alternative configurations of connections channels, according to aspects of this disclosure. FIG. 9 illustrates a connection channel segment 144' that has a linear cylindrical shape that extends between the distal ends 148 and 152 of the first and second channel segments 140 and 142 in a direction that is substantially perpendicular to the central longitudinal axis 10. FIG. 10 illustrates a connection channel segment 144" that includes two cylindrical shaped channels (not shown) that intersect at their respective distal ends forming an angled shape when viewed from the side of the fixation element 100. The connection channel segment 144 may have a cross-section that is substantially the same as one or both of the cross-sections of the first distal channel portion 158 and the second distal channel portion 162.

The fixation element 100 may be manufactured either by conventional machining or via 3D computer-assisted drawing (CAD) instructions sent to a 3D printer. Using traditional manufacturing techniques, the first and second channel segments 140 and 142 may be, for example, drilled through the screw from the proximal end 103 toward the distal end 101. Similarly, the fenestrations 114 may be drilled through the external surface 102 of the fixation element 100 to the respective first or second channel segment 140 and 142. The connection channel segment 144 may be produced by, for example, drilling through a location on the external surface 102 of the fixation element 100 through the distal ends 148 and 152 of the first and second channel segments 140 and 142. After the connection channel segment 144 is drilled, the opening to the external surface 102 formed by the drilling may be filled in (e.g. plugged) so that the distal ends 148 and 152 and the connection channel segment 144 do not open to the external surface 102 of the shaft 105 through the drilled opening. For example, as illustrated in FIG. 10, the angled connection channel segment 144" includes plugs 170 to substantially prevent fluid flow from the distal ends 148 and 152 to the external surface 102. Alternatively, as illustrated in FIG. 11, the opening to the external surface 102 of the shaft 105 formed by the drilling may remain open forming another aperture so that the distal ends 148 and 152 and the connection channel segment 144 do open to the external surface 102 of the shaft 105 through the drilled opening.

The fixation element 100 may be manufactured using 3D printing techniques. For example, the first channel segment 140, the second channel segment 142, and the connection channel segment 144 may include complex geometries that may be challenging to manufacture using traditional techniques. The fixation element 100 may be manufactured by laying down and/or modifying successive layers or dots of material under computer control, thereby forming the channel segments 140, 142, and 144 in desired configurations. It will be appreciated that secondary machining may also be required to manufacture the fixation element 100.

During operation, the fixation element 100 is secured to a bone by inserting the fixation element 100 through an incision in the skin and tissue, contacting the tip region 106 with the bone, and rotating the fixation element 100. A rotational drive (not shown) may be attached to the proximal end 103 of the fixation element 100 to facilitate rotation. The rotational driver may include, for example, a Robertson driver, a slotted driver, a Phillips driver, a triple square driver, a polydrive driver, a one-way clutch driver, a double hex driver, or other type of driver configured to rotate the fixation element 100. The rotational driver may be rotated clockwise or counterclockwise (depending upon the thread directions of the tip region 106 and threaded portion 108) to tighten the fixation element 100 into a final or near-final position.

The rotational driver is removed after the fixation element 100 is positioned on the bone. A manifold (not shown) may then be positioned on the head 104 of the fixation element 100 for receiving an air pressure source 200 (see FIG. 3). The air pressure source 200 may be coupled to one of the openings 116 of the fixation element 100 so as to create an air pressure differential between the first channel segment 140 and the second channel segment 142. The air pressure source 200 may include, for example, an aspiration pump configured to provide a suction force to the opening 116 drawing a negative pressure, or a pressure pump configured to provide a pressure force for a pressurized delivery (e.g. deliver positive pressure) of a fluid through the opening 116.

Figure 12:
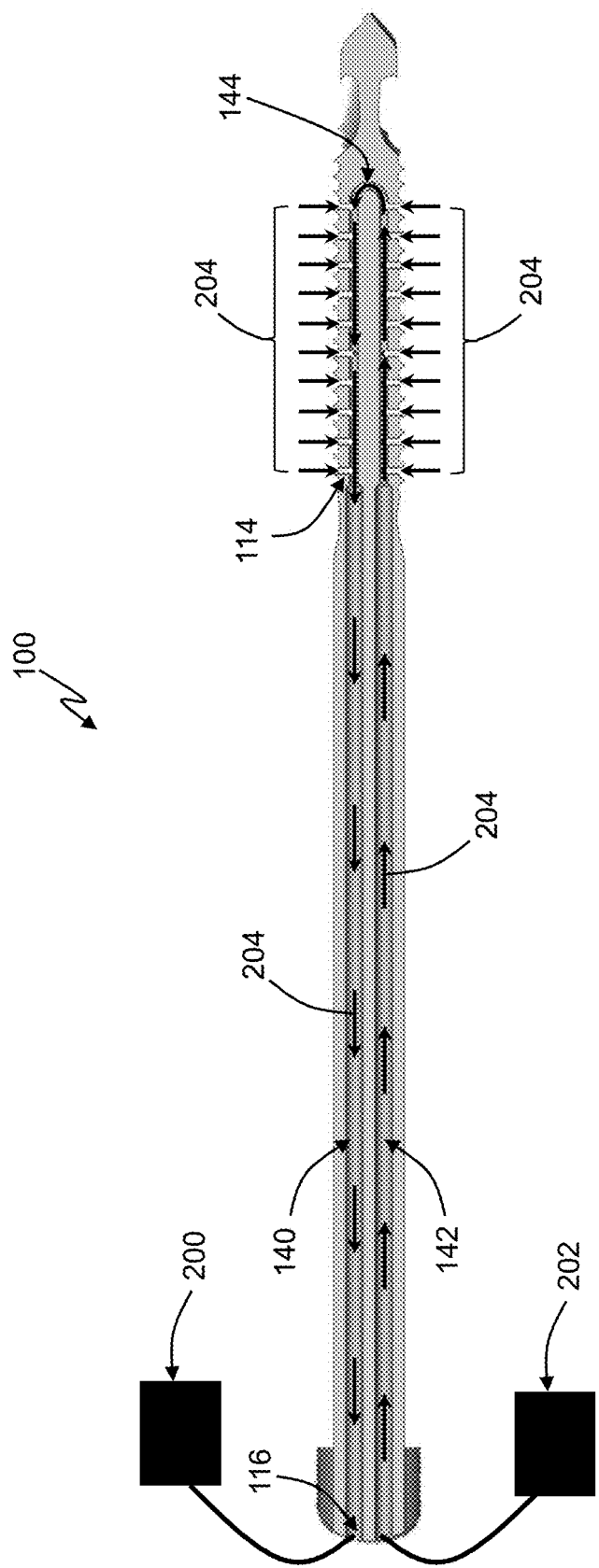
FIG. 12 is a side view of a cross section of the bone screw taken along line 7-7 of FIG. 6 showing a fluid flow pattern, according to an aspect of this disclosure.

FIG. 12 illustrates the air pressure source 200 (e.g. aspiration pump) coupled to the opening 116 of the first channel segment 140, and a fluid medium 202 is fluidly coupled to the other opening 116 corresponding to the second channel segment 142. The fluid medium may include, for example, an unpressurized "clean" fluid. During use of the aspiration pump, the fluid medium is drawn through the opening 116 of the second channel segment 142, the second channel segment 142, the connection channel segment 144, and the first channel segment 140, and out through the opening 116 coupled to the aspiration pump. FIG. 12 illustrates the flow path of the fluid with the arrows 204 shown within the connection channel segment 144, the first and second channel segments 140 and 142, and outside of the openings 114. As the fluid medium flows through the fixation element 100, a venturi effect occurs. The venturi effect causes an increase in velocity of the fluid medium within the reduced diameter portions of the first distal channel portion 158 and the second distal channel portion 162 of the first channel segment 140 and the second channel segment 142, respectively. The increase in velocity results in a fluid pressure drop and a suction force applied to the openings 114 causing a suction through the openings 114 and into the first distal channel portion 158 and the second distal channel portion 162. The suction through the openings 114 facilitates the removal of necrotic and decomposing tissue and other fluids near the location on the bone and soft tissue where the fixation element 100 is positioned. After the tissue is drawn into the first distal channel portion 158 and the second distal channel portion 162, the tissue flows out of the fixation element 100 through the first proximal channel portion 156 by the suction force provided by the aspiration pump.

In an aspect, the second distal channel portion 162 may have a diameter that is substantially the same size as the diameter of the second proximal channel portion 160. In this aspect, the second proximal channel portion 160 may not have any openings 114 extending to the external surface 102. Instead, the openings 114 may only extend from the reduced diameter first distal channel portion 158. The increased velocity of the fluid medium and the suction through the openings 114 occurs within the first distal channel portion 158.

After the necrotic and decomposing tissue has been removed, the aspiration pump and the fluid medium 202 may be disconnected from the fixation element 100. It will be appreciated that a cap (not shown) may be coupled to the proximal end 103 of the fixation element 100 to prevent infection risk by impeding a direct path from the environment to the screw insertion site.

Figure 13:
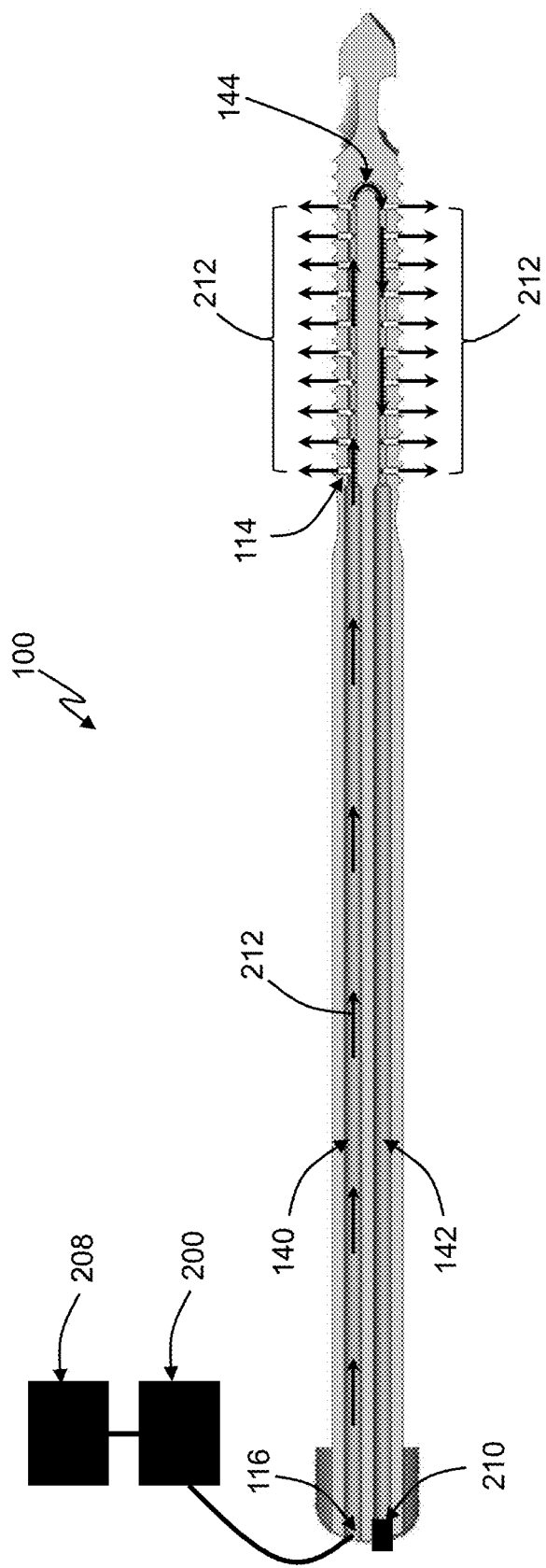
FIG. 13 is a side view of a cross section of the bone screw taken along line 7-7 of FIG. 6 showing another fluid flow pattern, according to an aspect of this disclosure.

The fixation element 100 may also be used for the application of an antibiotic directly to the pin tract for infection prevention and/or treatment. The air pressure source 200 (e.g. pressure pump) with the fluid antibiotic may be coupled to the opening 116 of the first channel segment 140, and a flow restrictor or plug 210 may be coupled to the other opening 116 corresponding to the second channel segment 142. The fluid medium may include, for example, a liquid form of the antibiotic. Prior to coupling the flow restrictor 210 to the opening 116 of the second channel segment 142, the antibiotic is pumped through the opening 116 of the first channel segment 140, the first channel segment 140, the connection channel segment 144, and the second channel segment 142, and out through the opening 116 of the second channel segment 142 into a fluid receiving container. After the antibiotic is pumped through the fixation element 100 and exits through the opening 116 of the second channel segment 142, the flow restrictor 210 is coupled to the opening 116 corresponding to the second channel segment 142. The flow restrictor 210 substantially prevents the antibiotic from exiting the fixation element 100 through the opening 116 of the second channel segment 142, and forces the antibiotic through the openings 114 in the first and second distal channel portion 158 and 162. FIG. 13 illustrates the flow path of the fluid with the arrows 212 shown within the connection channel segment 144, the first channel segment 140, and outside of the openings 114.

In an aspect, prior to pumping the antibiotic through the fixation element 100, a fluid medium, such as a "clean" fluid, may be pumped through the fixation element 100. After the fluid medium exits the screw through the opening 116 of the second channel segment 142, the flow restrictor is coupled to the opening 116 corresponding to the second channel segment 142. At this point, the fluid medium may be replaced by the antibiotic, which can be pumped through and out of the fixation element 100 through the openings 114.

In an alternative aspect, multiple pumps may be coupled to the proximal end 103 of the fixation element 100. For example, a first pump may be coupled to the opening 116 corresponding to the first channel segment 140, and a second pump may be coupled to the opening 116 corresponding to the second channel segment 142. In this aspect, the antibiotic may be pumped into both the first and second channel segments 140 and 142 and out of the fixation element 100 through the openings 114. Any air and/or gas trapped in the first and second channel segments 140 and 142 could escape through the openings 114 and the pin tract itself. Alternatively, the first pump may pump the antibiotic (or fluid medium as described in the previous paragraph) through the first and second channel segments 140 and 142 until both the first and second channel segments 140 and 142 are substantially filled with antibiotic. Then the second pump may be coupled to the opening 116 corresponding to the second channel segment 142. In this aspect, the air and/or gas within the first and second channel segments 140 and 142 would be substantially removed prior to the first and second pumps pumping the antibiotic through the openings 114.

The fixation element 100 may be used in a variety of applications, including, but not limited to, repair a fracture or other bone defect, facilitate dental implants, repair fractures near joints, for use with other internal or external fixation elements, reattachment of ligaments or tendons, or anterior cruciate ligament (ACL) reconstruction.

It will be appreciated that the foregoing description provides examples of the disclosed system and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

What is claimed is:

1. A bone fixation element comprising:
a tip region configured to be driven into bone, wherein the tip region defines a distal end of the bone fixation element; and
a shaft that extends from the tip region in a proximal direction, the shaft and tip region defining an external surface,
wherein the bone fixation element defines 1) first and second channel segments each having a first end open to the external surface of the shaft, and a second end opposite the first end that is closed with respect to the external surface of the tip region, and 2) a connection channel segment that extends from the first channel segment to the second channel segment so as to place the first channel segment in fluid communication with the second channel segment, and
wherein the bone fixation element further defines at least one aperture that extends from at least one of the first and second channel segments to the external surface so as to place at least one of the first and second channel segments in fluid communication with an external environment of the bone fixation element.

2. The bone fixation element of claim 1, wherein each of the first and second channel segments has a proximal portion that defines the first end, and a distal portion that defines the second end, the proximal portion has a proximal cross-sectional area, and the distal portion has a distal cross-sectional area that is less than the proximal cross-sectional area.

3. The bone fixation element of claim 2, wherein the first channel segment is substantially parallel to the second channel segment.

4. The bone fixation element of claim 2, wherein the bone fixation element is elongate along a central axis that extends from the distal end to a proximal end of the bone fixation element, and the cross-sectional areas are measured in respective planes that are oriented substantially perpendicular to the central axis.

5. The bone fixation element of claim 4, wherein the first channel segment is substantially symmetric to the second channel segment along the central axis of the bone fixation element.

6. The bone fixation element of claim 1, wherein the external surface is substantially circular in cross section.

7. The bone fixation element of claim 1, wherein the shaft further defines a threaded region, and at least one of the apertures is disposed at the threaded region.

8. The bone fixation element of claim 1, wherein the first and second channel segments and the connection channel segment are defined by a single channel.

9. The bone fixation element of claim 1, wherein the first and second channel segments and the connection channel segment are defined by separate channels, respectively.

10. The bone fixation element of claim 1, wherein the connection channel segment extends from a first location on the external surface, through at least one of the first and second channel segments.

11. The bone fixation element of claim 10, wherein the connection channel segment extends from the first location of the external surface, through each of the first and second channel segments to a second location on the external surface, the second location being at a location that is different than the first location.

12. The bone fixation element of claim 11, wherein the connection channel segment is substantially straight and linear, and wherein the first and second locations are aligned with each of the first and second channel segments along a straight linear direction.

13. The bone fixation element of claim 11, wherein the connection channel segment is angled such that an angle of at least a portion of the connection channel segment is offset from at least one of the first and second channel segments.

14. The bone fixation element of claim 1, wherein the connection channel segment extends from the second end of the first channel segment to the second end of the second channel segment.

15. The bone fixation element of claim 14, wherein the connection channel segment curves distally from the first channel segment toward the second channel segment to an apex location, and curves proximally from the apex location to the second channel segment.

16. The bone fixation element of claim 15, wherein the apex location is located on the central axis, and wherein the apex location is located within the tip region.

17. The bone fixation element of claim 2, wherein the first channel segment and the second channel segment are configured such that when a suction force is applied to the first end of the first channel segment to pull a first fluid through the bone fixation element from the second channel segment a venturi effect occurs that causes 1.) a velocity of the first fluid within the distal portion of the first channel segment to be greater than a velocity of the first fluid in the proximal portion of the second channel segment and 2.) draws a second fluid into the distal portion of the first channel segment through the at least one aperture.

18. A bone fixation system comprising:
the bone fixation element of claim 1; and
an air pressure source configured to connect to one of the first and second channel segments so as to create an air pressure differential between the first channel segment and the second channel segment.

19. The bone fixation system of claim 18, wherein the air pressure source is configured to draw negative pressure from the one of the first and second channel segments.

20. The bone fixation system of claim 18, wherein the air pressure source is configured to deliver positive pressure to the one of the first and second channel segments.

21. A method of infection prevention using a screw, the screw including a first channel, a second channel, a connection channel extending between a distal end of the first channel and a distal end of the second channel, and at least one fenestration extending from at least one of the first channel and the second channel to an outer surface of the screw, the method comprising:
providing a suction force to a proximal end of the first channel to pull a first fluid through the screw from the second channel, wherein the suction force causes a venturi effect to occur within the screw that draws a second fluid into the first channel through the at least one fenestration.

22. The method of claim 21, further comprising:
prior to providing the suction force, securing a distal end of the screw to a bone.

23. The method of claim 22, wherein the second fluid comprises necrotic tissue and related bodily fluids.

24. The method of claim 21, further comprising:
pumping a third fluid into the proximal end of the first channel such that at least a portion of the third fluid exits the screw through the at least one fenestration.

25. The method of claim 24, further comprising:
during the pumping of the third fluid, at least partially preventing the third fluid from flowing through the second channel.

26. The method of claim 21, wherein the first channel includes a first proximal channel portion extending from the proximal end of the first channel toward the distal end of the first channel, and a first distal channel portion extending from the first proximal channel portion to the distal end of the first channel, wherein a diameter of the first proximal channel portion is greater than a diameter of the first distal channel portion, and wherein one of the at least one fenestrations extends from the first distal channel portion of the first channel.

\* \* \* \* \*